United States Patent [19]

Fischer et al.

[11] Patent Number: 5,641,647
[45] Date of Patent: Jun. 24, 1997

[54] SERUM FREE MEDIUM

[75] Inventors: Dina Fischer; Moshe Bracha, both of Rehovot, Israel

[73] Assignee: Interpharm Laboratories Ltd., Ness Ziona, Israel

[21] Appl. No.: 111,428

[22] Filed: Aug. 24, 1993

[30] Foreign Application Priority Data

Aug. 24, 1992 [IL] Israel .......................................... 102929

[51] Int. Cl.$^6$ .............................. C12N 15/00; C12N 5/06; C12N 5/16
[52] U.S. Cl. .......................... 435/69.1; 435/406; 435/395
[58] Field of Search .......................... 435/240.31, 240.3, 435/69.1, 240.2

[56] References Cited

U.S. PATENT DOCUMENTS 5,256,766  10/1993  Coughlin ................................. 530/327
5,316,938   5/1994  Keen et al. ........................... 435/240.31

OTHER PUBLICATIONS

Jo, E.C. et al, *Biotechnol. Bioeng.*, 38(3):247–53, 1991.

White, M.D. (ed.) *Biologicals from Recombinant Microorganisms and Animal Cells*, Balaban Publishers, New York, pp. 187–197 (Kadouri Chapter Author.), 1991.

*Primary Examiner*—Marianne P. Allen
*Attorney, Agent, or Firm*—Browdy and Neimark

[57] ABSTRACT

A serum free medium capable of supporting production of mammalian cell products is provided. The medium comprises a basic medium and a cell viability protection agent, insulin and thrombin or a thrombin receptor activator.

23 Claims, 7 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Ser Phe Leu Leu Arg Asn Pro Asn Asp Lys Tyr Glu Pro Phe
 1               5                   10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Ser Phe Phe Leu Arg Asn Pro Gly Glu Asn Thr Phe Glu Leu
 1               5                   10
```

SERUM FREE MEDIUM

FIELD OF THE INVENTION

The present invention relates to a serum-free medium which is capable of supporting production of mammalian cell products, such as proteins obtained by recombinant methods.

BACKGROUND OF THE INVENTION

Cell culture is widely used today for the production of various biologically active products, such as viral vaccines, monoclonal antibodies, non-antibody immunoregulators, polypeptide growth factors, hormones, enzymes, tumor specific antigens, etc. These products are produced by normal, transformed and genetically engineered cells.

For culturing of cells, it is essential to supplement the culture medium with serum, which serves as a universal nutrient for the growth of all cell lines, as well as for the production of most biologically active products. Serum contains hormones, growth factors, carrier proteins, attachment and spreading factors, nutrients, trace elements, etc. Culture medium usually contains up to about 10% of animal serum, such as fetal bovine serum (FBS).

Although widely used, serum has many limitations. It contains high levels of numerous proteins which interfere dramatically with the small quantities of the desired proteins produced by the cells. These serum proteins must be separated from the product during downstream processing which complicates the process and increases the cost. Another limitation is the serum batch-to-batch inconsistencies, resulting in serious regulatory concern about various serum protein contamination in the product.

Recently the advent of BSE (Bovine Spongiform Encephalopathy), a transmissible neurodegenerative disease of cattle with a long latency or incubation period, has further raised regulatory concerns about using animal-derived sera in the production of biologically active products.

A further shortcoming of employing animal sera, such as FBS, is its unsteady supply due to the increase in demand, which in turn causes upwards fluctuations in its price.

There is therefore a great demand for the development of an alternative medium supplement to support cell growth and production of biologically active products.

The advantages and disadvantages of serum-free culture for the manufacture of recombinant biopharmaceuticals from mammalian cells has been thoroughly reviewed (Barnes, 1987; Barnes & Sato 1980; Broad, et al., 1991; Jayme, 1991). The list of the main additives which are used as supplements for serum-free media is summarized by Barnes (1987) and Barnes & Sato (1980).

Unlike serum-supplemented medium, which may be utilized for a broad range of cell types and culture conditions, serum free formulations are generally highly-specific (Barnes, et al. 1984, Sato, et al. 1982, Taub, 1985, Weiss, et al., 1980).

Most commercially available serum-free media contain carrier protein, such as albumin. The presence of carrier protein might be required for protection of the cell viability, but has the afore-mentioned disadvantages for the purification process.

CHO cells have emerged as an appropriate recipient mammalian host to accommodate transfection and expression of a variety of foreign gene products for potential diagnostic and therapeutic applications (Familletti and Fredericks, 1988, Marino, 1989).

A number of commercial serum-free media are available for CHO cell culturing. However, these suffer from multiple disadvantages. Most are suitable for small-scale laboratory applications but become too expensive for large-scale bioreactors. Some are appropriate for cell growth, but perform poorly as production medium. Each of these media might be suitable for the specific system for which it was developed, but cannot usually be used in other systems.

One known serum free culture medium (U.S. Pat. No. 5,063,157) for non-adherent mammalian cells comprises, in addition to the base medium, transferrin, insulin, a peptone, a beta-D-xylopyranose derivative, selenite and a biological polyamine. The only disclosure in the above patent relating to production concerns culturing of specific mouse hybridoma cells in a medium, which, in addition to the base medium, contains six ingredients. Production in any other mammalian cell of a biologically active product, other than an FSH antibody, is not taught.

Another serum free cell growth medium for mammalian cells is disclosed in U.S. Pat. No. 4,443,546. This growth medium, in addition to the basic medium, contains seven ingredients.

European patent specification No. 481,791 discloses a culture medium for CHO cells comprising water, an osmolality regulator, a buffer, an energy source, amino acids, an iron source, a growth factor and other optional components. The two media exemplified contain 19 and 17 components, respectively.

The major objectives in development of a serum-free medium for large-scale production are: a serum-free, protein-free (or low protein), defined medium with minimal additives resulting in a lower cost, effective medium, which does not contain ingredients that are likely to complicate the culturing/production/purification process steps.

If proteins are nevertheless present in the medium, it is preferred that they are obtained by recombinant means and not isolated directly from an animal source.

Although the list of known potential additives to serum free media is very long, the correct combination has not yet been found in many cases. Indeed, there are only about 40 commercial serum-free media on the market, despite the fact that the need therefor has been known for more than a decade.

SUMMARY OF THE INVENTION

It has now been found in accordance with the present invention that a serum-free medium for mammalian cells capable of supporting production needs to include only a minimal amount of additives to a basic medium.

The present invention provides a serum-free medium for mammalian cells comprising a basic medium and (a) a cell viability protection agent, (b) insulin, and (c) either thrombin or a thrombin receptor activator.

The thrombin receptor activator (hereinafter "TRA") is a peptide comprising a region of the receptor which becomes the N-terminus after thrombin activates the receptor by cleavage near its native N-terminus.

The serum-free medium according to the invention supports mammalian cell production of biologically active products to an extent comparable to the one of serum.

The basic medium may comprise any known such medium, for example DMEM, F12, RPMI 1640, or mixtures thereof, all of which are commercially available, e.g. from Gibco, U.S.A. or Boehringer Mannheim, Germany.

The cell viability protection agent may comprise ADC-1 (Biological Industries, Beit Haemek, Israel), a protein hydrolysate, methyl cellulose or the like.

The insulin and thrombin employed are preferably prepared by recombinant methods.

Protein hydrolysates: The use of peptides as growth factors in mammalian cell culture has been described in a review by Rutsky (1981). Other hydrolysates, e.g. lactalbumin hydrolysate are also used as medium supplements (Grace, 1962)

Methyl Cellulose was added to culture medium as a non-nutrient supplement which is known to be beneficial to cultured cells (Hink, 1991).

Insulin is employed as an additive in a number of serum-free media as it is known to act as a growth factor on all cell types.

Thrombin and Thrombin Receptor Activator: In addition to its role in blood clotting, thrombin was found to bind to various cells through specific receptors and generate signals. On platelets, there are at least two thrombin binding sites (Workman, 1977). Stimulation of the platelets serves as part of the clotting process. However, thrombin also binds with high and low affinity to endothelial cells (Awbrey, 1979, Machovich, 1982; Bauer, 1983), resulting in prostacyclin release (Weksler, 1978), protein kinase activation (Owen, 1981) and inhibition of plasminogen activator activity (Luskutoff, 1979).

In fibroblasts, thrombin stimulates DNA synthesis and cell division (Zetter et al. 1977, Glenn et al. 1980; Chen, 1981; Cunningham et al. 1979). The binding of thrombin to human fibroblasts also stimulates the production and release of a surface-associated glycoprotein, fibronectin (Mosher & Vaheri, 1978).

Thrombin is known to activate cells like platelets via a specific receptor. Recently it was suggested by Vu et al. (1991) that the mechanism of activation involves the cleavage of the receptor, and it was proposed that the newly generated N-terminal region of the receptor then acts as a tethered ligand. A synthetic peptide, with a sequence corresponding to the new N-terminal region, can replace the thrombin in platelet activation.

DETAILED DESCRIPTION OF THE INVENTION

The present invention provides a serum-free medium which is suitable for use in the production of mammalian cell products, contains a minimum amount of additives and lends itself to simple preparation, either by conventional methods, or by a combination of conventional and recombinant methods.

As stated hereinbefore, all of the components of the serum free medium according to the invention are known per se and commercially available, therefore they are easily accessible.

In accordance with one embodiment of the invention, the serum free medium is prepared in a conventional manner by simply admixing the different components with the basic medium. Thus, for example 20 ml of ADC-1 (concentrated 1×50) are added to 980 ml of basic medium. To this between 0.1 µg/ml and 2 µg/ml of insulin and between 0.01 µg/ml and 2 µg/ml of thrombin are added.

Insulin and thrombin may be produced by conventional recombinant methods, e.g. by cloning of the cDNA, isolation of DNA fragments coding for the mature processed proteins, construction of expression vectors suitable for expression in E. coli, and expression.

As stated above, ADC-1 may be replaced with a different cell viability protection agent, such as a protein hydrolysate. Suitable hydrolysates are, e.g. lactalbumin hydrolysate, corn gluten hydrolysate or similar. Thus, in accordance with another embodiment of the invention, the serum free medium comprises 10 ml of 10% of lactalbumin hydrolysate or 10 ml of 5% of corn gluten hydrolysate, which are added to 900 ml of the basic medium. In addition, between 0.1 µg/ml and 2 µg/ml of insulin and between 0.01 µg/ml and 2 µg/ml of thrombin are added. Corn gluten hydrolysate is preferred for regulatory reasons, since it is not of animal origin.

In accordance with another embodiment of the invention, the genes for the expression of insulin and thrombin are inserted into the mammalian cells employed for the recombinant production of the biologically active cell products. Suitable promoters which direct the expression of thrombin and insulin are cotransfected with the genes encoding these proteins, with the appropriate construction to enable their secretion.

The cells employed were CHO (Chinese Hamster Ovary) cells transformed with various genes fused to an SV40 early promoter. (Chernajovsky, 1984). The genes were those encoding IL-6, TBP-I and rIFN-β (recombinant interferon-β), however any other gene suitable for expression in mammalian cell systems may be used. Since the particular CHO mutant employed for transfection is proline dependent, it was necessary to supplement the basic medium employed with proline.

As stated hereinbefore, thrombin is believed to activate its receptor by cleaving it in the amino-terminal extracellular domain exposing a new N-terminus. Peptides of different lengths which correspond to the sequences of the new thrombin receptor N-terminus (after cleavage) were found to be suitable for use in the serum free medium according to the invention. This use simplifies preparation of the serum free medium, since short peptide sequences lend themselves easily to synthesis by either chemical or recombinnat methods. This also avoids using commercial thrombin itself, which due to its mammalian origin, may lead to regulatory problems.

The invention will be illustrated by the following non-limiting examples:

EXAMPLE 1: Cell growth and production

Cell growth and production was carried out in the following systems:

A) In 24-well plates, cells ($0.25 \times 10^6$/well) were seeded in 1 ml medium supplemented with 10% FBS. After overnight incubation at 37° C., the medium was removed and the cell monolayer rinsed twice with serum-free medium (SFM). Cell growth or production level was then monitored in the various media compositions over 3-5 days with medium changes every 24 hours.

B) In 25 cm$^2$ tissue culture flasks, cells ($0.5 \times 10^6$ cells/flask) were seeded in medium supplemented with 10% FBS and incubated for 3 days before the growth medium was replaced by production medium.

C) In spinners, production was monitored in 100-ml and 1-liter spinners (Bellco). The cells were attached to microcarriers. Most experiments were performed with disc-carriers (6 mm discs, constructed of non-woven polyester fabric, laminated to a polypropylene screen (Sterilin, U.K.). In some experiments, the carriers were Biosilon (Nunc, Roskilde, Denmark). Cells were seeded in medium supplemented with 10% FBS and after a growth period of 2-3 days, the medium was changed to serum free production medium. At the initiation of the production period, medium was changed every 24 hours and after a few days, medium changes were performed every 12 hours.

EXAMPLE 2: Formulation of a basic Serum free medium (SFM)

IL-6 producing recombinant CHO cells survive and multiply well in DMEM, supplemented with proline and 2% FBS. Removal of the serum from the medium results in cell death unless the serum is substituted with an appropriate supplement.

As summarized in Table 1, addition of a cell viability protection agent, e.g. ADC-1 (Biological Industries, Beit Haemek, Israel), maintained the cell viability (after initial adherence in the presence of FBS or Fibronectin) with very little cell growth. Cell division can be stimulated by insulin, and in medium supplemented with both ADC-1 and insulin, the cells grow as well as in medium supplemented with FBS. However, in the absence of serum, the ability of the cells to produce IL-6 declines with time, and after 5 days in the serum-free medium, the specific productivity of the cells (μg IL-6/$10^6$ cells) is reduced to half.

Figure 1:
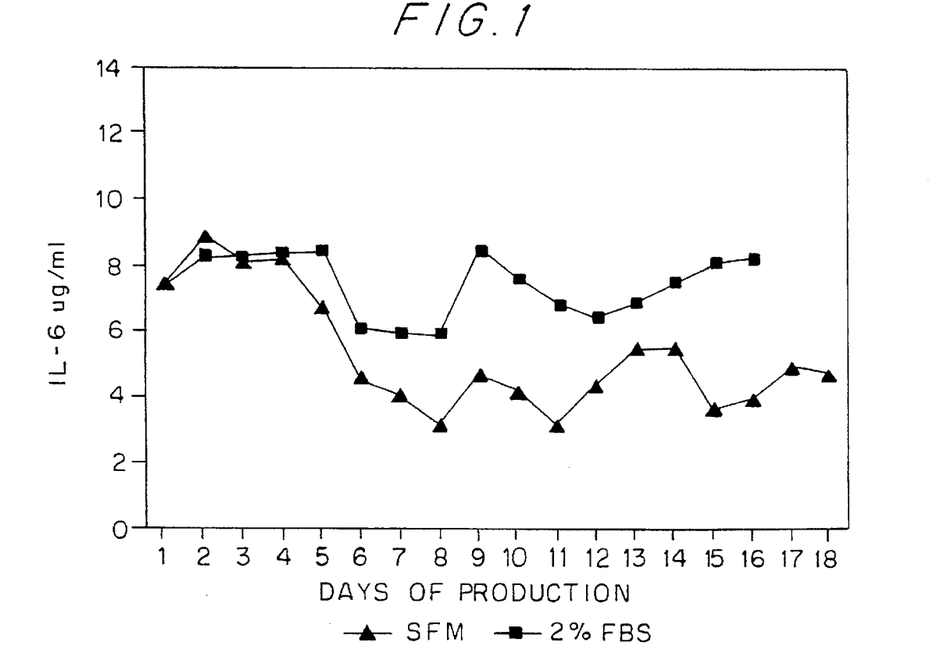
FIG. 1 illustrates the effect of medium composition on IL-6 production in spinners. IL-6 producing CHO cells were seeded in 100 ml spinners with disc-carriers. After seven days' growth in 10% FBS, the medium was replaced with production medium supplemented with either 2% FBS (*-*) or ADC-1+Insulin 0.2 µg/ml Serum free medium (SFM) [-]), IL-6 production was determined every 24 hours. The results are an average of two spinners.

The decline in the production ability of the cells is demonstrated both in tissue culture (TC) flasks (Table 1) and in spinners with disc-carriers (FIG. 1).

TABLE 1

Effect of medium composition on cell growth and IL-6 production.

| Production[a] Medium Supplements | Cells/Flask[b] (× $10^6$) | IL-6[b] (μg/ml) | IL-6 (μg/$10^6$ Cells) |
|---|---|---|---|
| 2% FBS | 4.45 | 1.18 | 1.32 |
| ADC-1 | 2.16 | 0.41 | 0.95 |
| ADC-1 + Insulin (0.2 μg) | 5.43 | 0.73 | 0.67 |

[a]IL-6 producing CHO cells were seeded in 25 cm$^2$ flasks (0.5 × $10^6$ cells/flask) in 10% FBS and incubated for 3 days before the medium was replaced by production medium.
[b]Cell number and IL-6 level were determined after 5 days of daily change of the production media. Cell number does not include the non-adhered cells which were washed off with the medium changes.

EXAMPLE 3: Effect of thrombin on production

Figure 2:
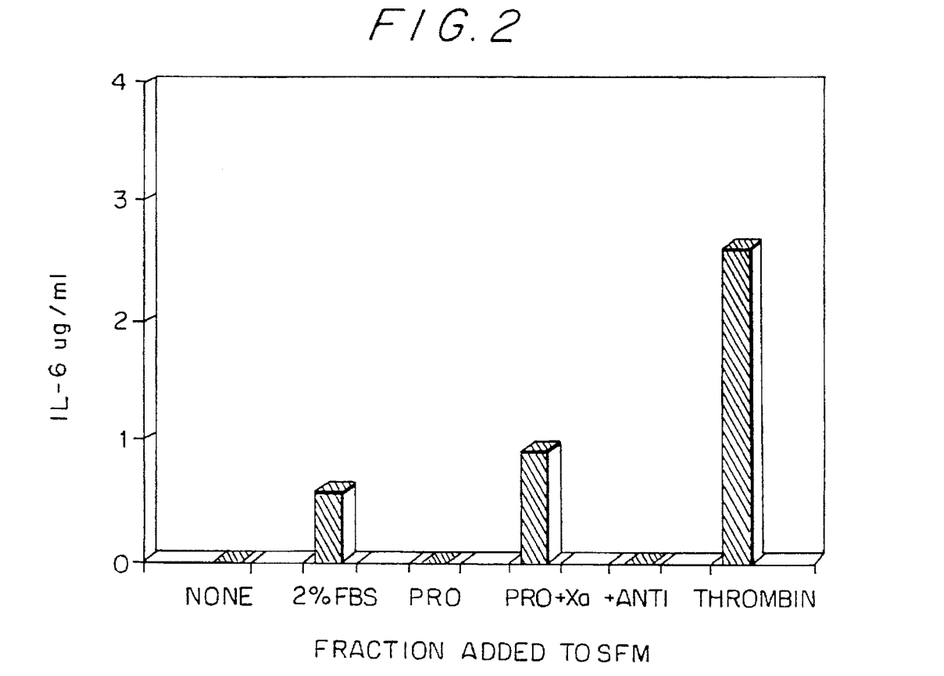
FIG. 2 illustrates the effect of thrombin on IL-6 production stimulation in SFM. The various components were added to SFM and added to IL-6 producing CHO cells in 24-well plates.

When bovine thrombin (Sigma) was added to the basic SFM (DMEM+ADC-1+Insulin), IL-6 production was strongly enhanced (FIG. 2). Prothrombin did not affect the production. However, when the prothrombin was cleaved by active factor Xa to release thrombin, production was stimulated. The production stimulating activity was inhibited by the thrombin inhibitor, the serum protein antithrombin IV (FIG. 2).

EXAMPLE 4: The functional contribution of the growth factors

Figure 3A:
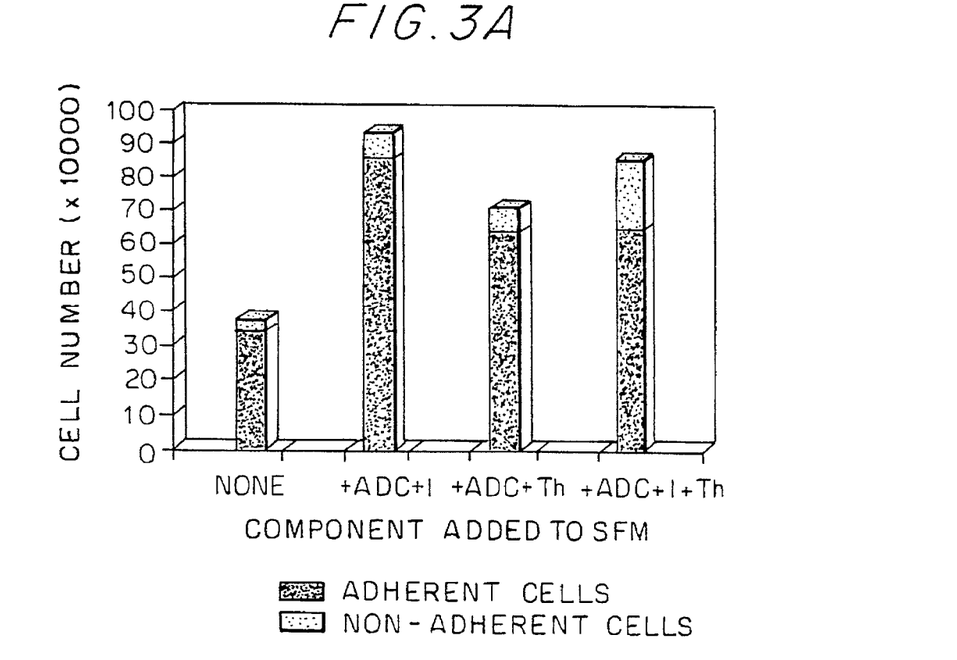
FIGS. 3A and 3B illustrate the effect of insulin and thrombin on cell growth and IL-6 production.
Figure 3B:
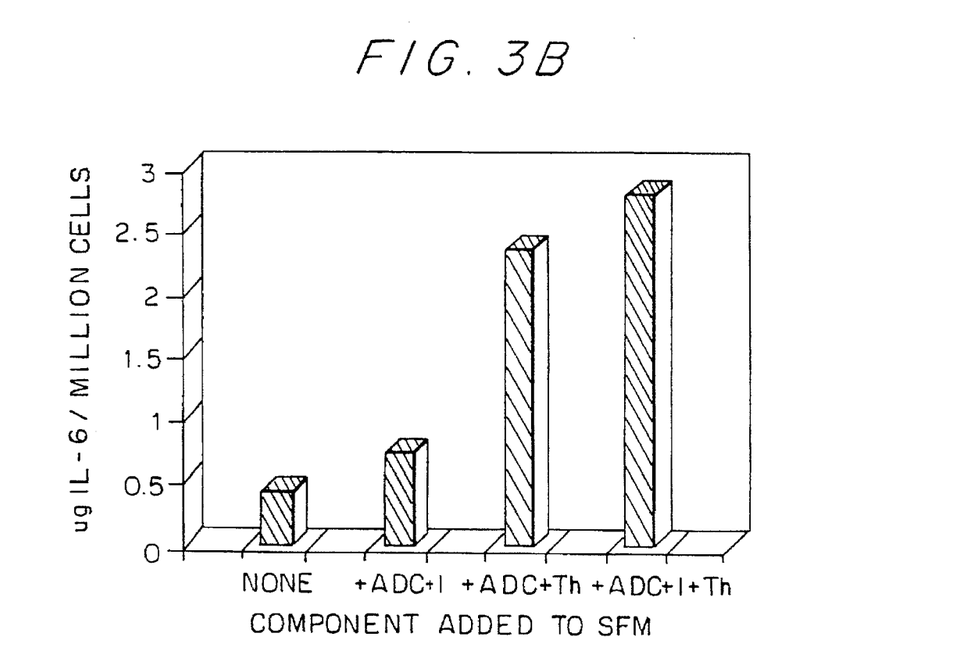
Figure 4:
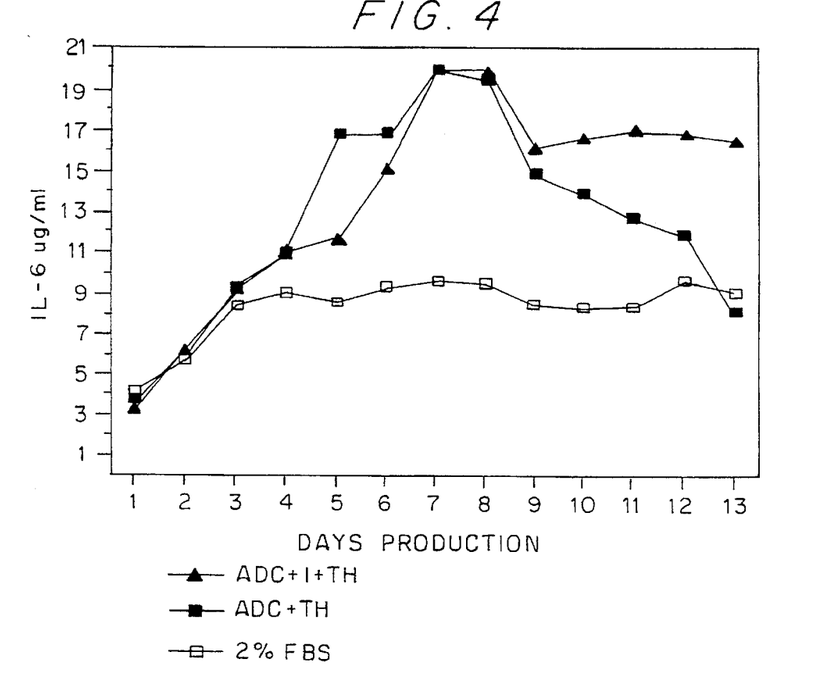
FIG. 4 shows the effect of insulin on IL-6 production in 100 ml spinners.

Both insulin and thrombin stimulate CHO cell growth. Addition of each one to medium containing ADC-1 resulted in a similar level of cell growth (FIG. 3A). However IL-6 production in the presence of insulin alone was very low, while thrombin stimulated the production level significantly (FIG. 3B). In the short-term experiment in wells (FIG. 3), the productivity with thrombin alone was only slightly improved when both insulin and thrombin were added to the ADC. However, when production was monitored in spinners (100 ml), the IL-6 level which was initially the same with or without insulin, clearly declined after 9 days in the absence of insulin (FIG. 4). These results suggest that insulin is required for optimal long term production.

Figure 5:
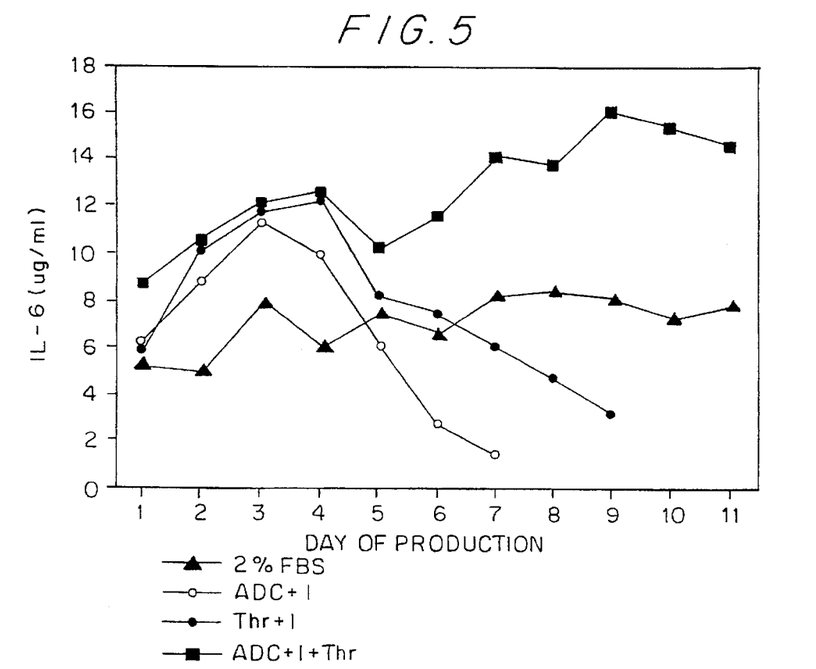
FIG. 5 shows the effect of ADC-1 and insulin on IL-6 production in 100 ml spinners.

In addition to insulin, both thrombin and ADC-1 are necessary to achieve maximum production as demonstrated in FIG. 5. Removal of either ADC or thrombin resulted in a decline in IL-6 level after 4 to 5 days of production.

EXAMPLE 5: Serum free medium for production

The medium composition which was found to support high levels of production of IL-6 by recombinant CHO cells includes three additives to the basic medium (DMEM+Proline):

1. ADC-1;
2. Insulin 0.2 μg/ml;
3. Thrombin 0.02 μg/ml.

Each of the components was analyzed for an optimal source and possible replacement.

Insulin

Most of the experiments were performed with bovine insulin from Sigma. Additional preparations were obtained from various sources and added together with ADC-1 to the basic medium to determine their potential. Both bovine and human insulin were examined. Recombinant human insulin which is used for human injections (Novo Nordisk, Denmark and Eli Lilly, SA., Switzerland) was of particular interest for regulatory reasons.

As summarized in Table 2, all the tested insulin batches had similar activity as growth factors for the CHO cells. Similar IL-6 production levels were also observed.

TABLE 2

Effect of insulin from different sources on cell growth and IL-6 production

| Insulin (0.4 μg/ml) | | Cells/Well[a] | IL-6 |
|---|---|---|---|
| Source | Company | (× 10⁶) | (μg/ml) |
| None | | 4.08 | 0.25 |
| Bovine | Sigma | 7.45 | 0.59 |
| Human (Recombinant) | Eli Lilly | 7.46 | 0.58 |
| Human (Recombinant) | Novo-Nordisk | 7.55 | 0.58 |

[a]IL-6 producing CHO cells were seeded in a 24-well plate (1 × 10⁶ cells/well). After 3 days, the medium was changed to SFM with or without insulin. Cells were counted and IL-6 level was determined after additional four days incubation.

Thrombin

The commercial thrombin that was used for the initial experiments was a bovine thrombin with a very low specific activity (50–100 IU/mg protein) which was obtained from Sigma. The thrombin was purified from this preparation by binding to Blue Sepharose column.

Figure 6:
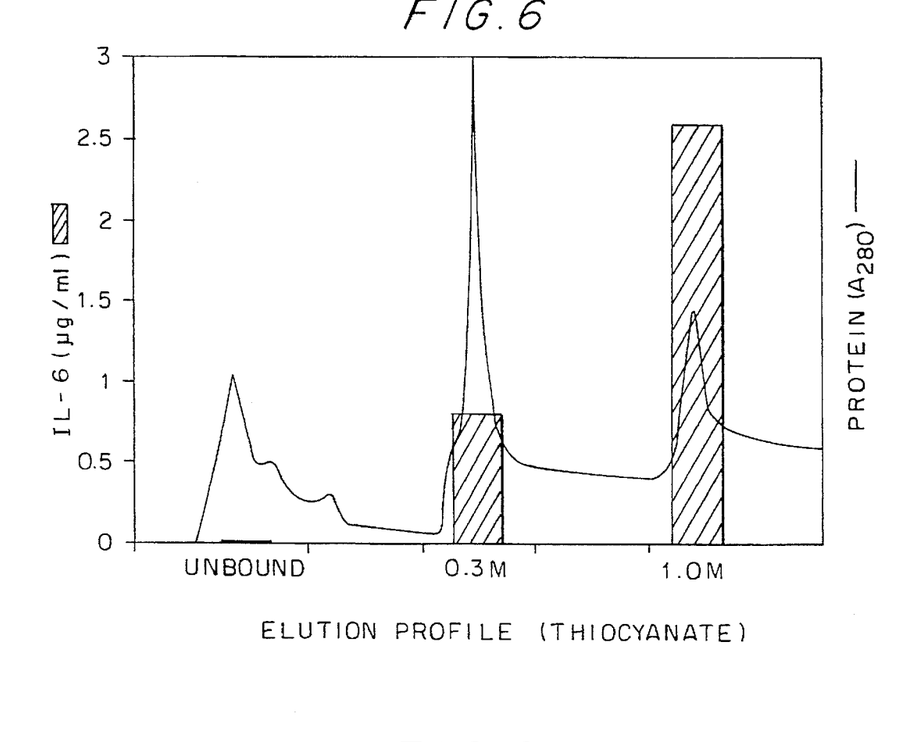
FIG. 6 shows the elution pattern of thrombin from a Blue Sepharose column which was loaded with commercial thrombin (Sigma) of low specific activity (50–100 IU/mg).
Figure 7:
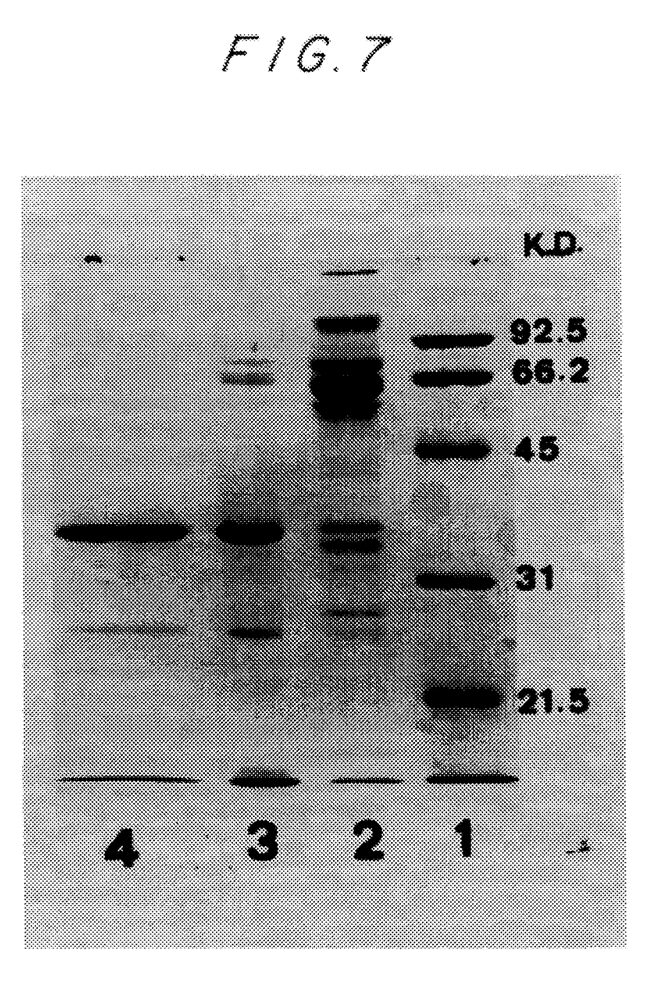
FIG. 7 shows the SDS-PAGE analysis of various thrombin preparations.

As summarized in FIG. 6, most of the activity was eluted in 1M thiocyanate while the majority of the proteins did not bind, or were washed with 0.3M of the salt. SDS-PAGE of the active fraction (FIG. 7, lane 3) revealed a major protein band with an apparent MW of 37K. Similar to the protein band of a commercial (Sigma) purified bovine thrombin with a specific activity of 2,000 IU/mg protein (FIG. 7, lane 4).

The Blue Sepharose active fraction (1.0M thiocyanate) of the Sigma bovine thrombin was used as an additive to SFM in 1 liter spinners for production. The thrombin was used at final concentration of 0.02 μg/ml in medium that was supplemented also with ADC-1 and insulin (0.2 μg/ml). Consistently high levels of production were observed for more than four weeks production (FIG. 8).

ADC-1

Figure 8:
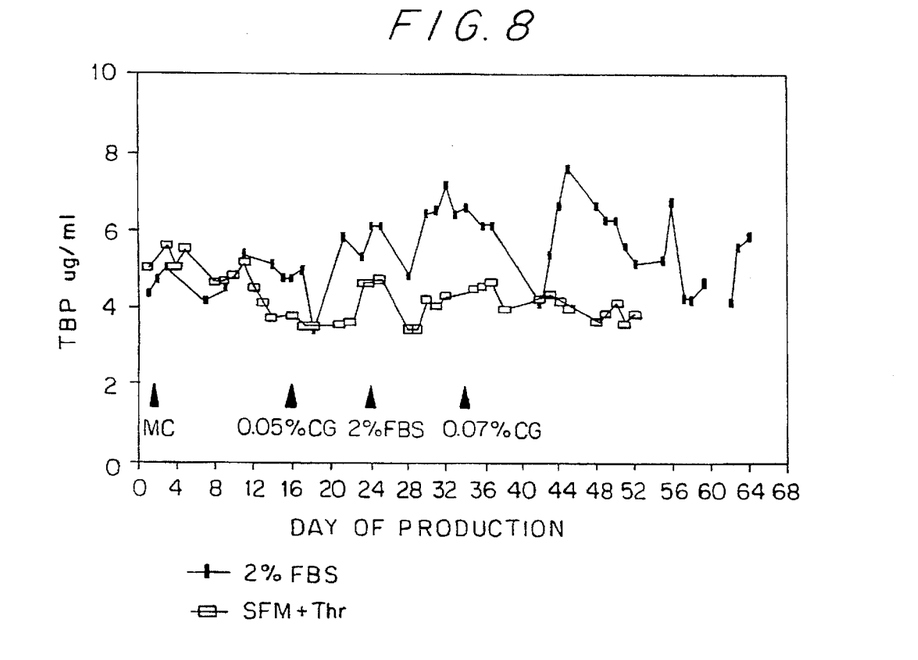
FIG. 8 shows TBP production in 1000 ml spinners.
Figure 9:
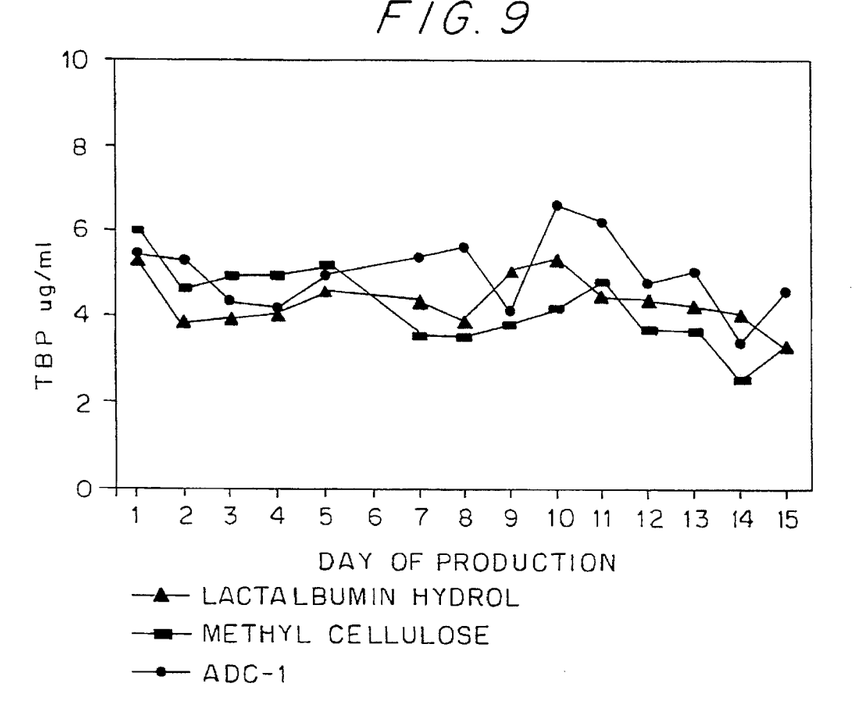
FIG. 9 illustrates TBP production in 100 ml spinners, comparing the effect of various cell viability protection agents to serum free medium containing insulin and thrombin.

The commercial protein free medium supplement (ADC-1) which was obtained from Biological Industries (Beit-Haemek, Israel) can replaced by protein hydrolysates such as lactalbumin hydrolysate (FIG. 9) or corn gluten hydrolysate (FIG. 8) or by methyl cellulose (FIG. 9).

The above components were added to the basic medium (DMEM+proline) with insulin and with purified thrombin (FIG. 8). The production level was similar with all the combinations as long as the three components were added to the medium.

The ADC-1 and the various substitutes are all autoclavable which is advantageous from regulatory aspects.

EXAMPLE 6: Versatility of the serum free medium

Most of the experiments were performed with IL-6 producing CHO cells. However production of other recombinant products was demonstrated in the medium supplemented with the three components ADC (or equivalent), insulin, and thrombin.

Figure 11:
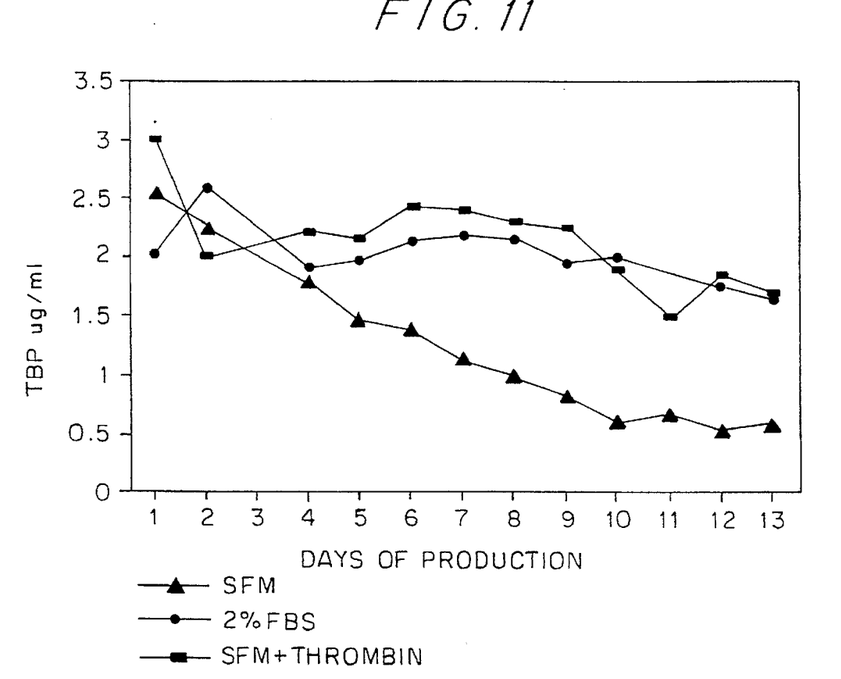
FIG. 11 illustrates the effect of medium composition on TBP production in 100 ml spinners.

Production of recombinant Tumor Necrosis Factor Binding Protein (TBP) by CHO cells was demonstrated in 100 ml spinners (FIG. 11). In the presence of the three components, ADC, insulin and thrombin, the production level was similar to that of cells producing in 2% FBS. In the absence of thrombin, production declined after 5 days.

Figure 12:
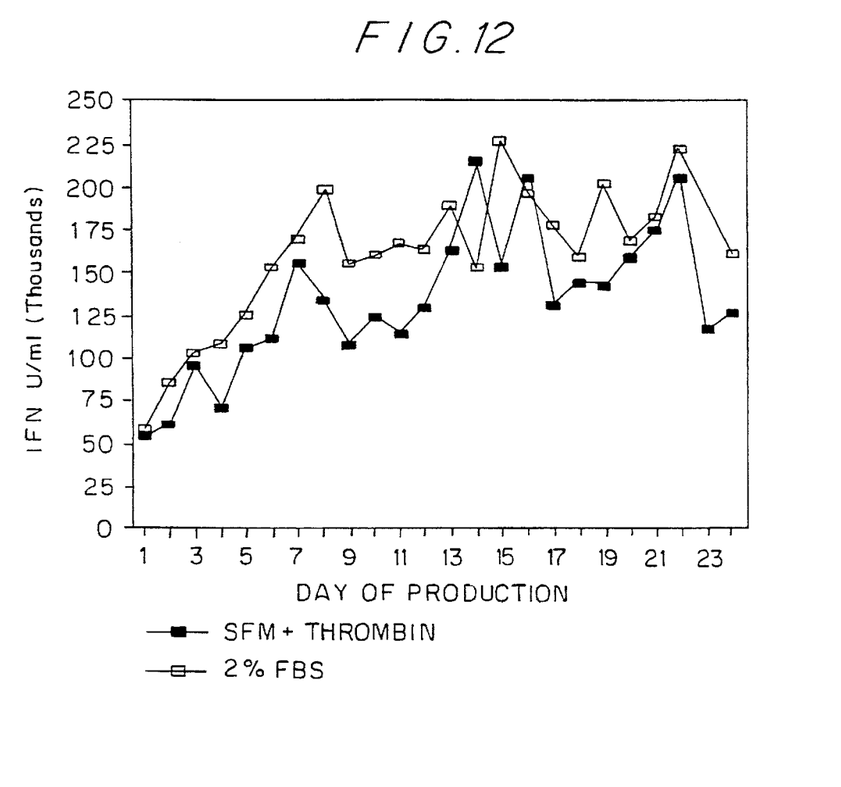
FIG. 12 illustrates rIFN-β production by CHO cells in 100 ml spinners.

Recombinant IFN-β was produced by CHO cells on biosilon microcarriers in 100 ml spinners. The level of production was the same in medium supplemented with 2% FBS or in serum free medium supplemented with ADC, insulin and thrombin (FIG. 12).

EXAMPLE 7:

A 14-residues amino acid peptide that mimics the new amino acid terminus of the thrombin receptor was examined for its ability to replace thrombin in IL-6 production stimulation activity. The peptide (H-Ser-Phe-Leu-Leu-Arg-Asn-Pro-Asn-Asp-Lys-Tyr-Glu-Pro-Phe-OH) (SEQ ID NO: 1) was obtained from two sources. A highly purified peptide (Thrombin Receptor Activator) was purchased from Bachem (Switzerland) and a crude preparation was synthesized at the Weizmann Institute of Science (Israel).

The two preparations were compared to thrombin as an ingredient of SFM in 24-well plates using IL-6 producing CHO cells.

As summarized in Table 3, IL-6 production was stimulated by the peptides to the same extent as by thrombin. However, a 1000-fold higher concentration was required when the peptide is used. As expected, the purified peptide was active at lower concentrations when compared to the crude preparation.

TABLE 3A

Effect of Thrombin Receptor Activator on IL-6 production

| Additive to Basic SFM | | IL-6 (μg/ml) |
|---|---|---|
| None | | 1.03 |
| 2% FBS | | 5.64 |
| Thrombin | 0.05 μg/ml | 5.98 |
| Thrombin Receptor Activator I* | 100 μg/ml | 5.34 |
| | 50 μg/ml | 4.50 |
| Thrombin Receptor Activator II** | 40 μg/ml | 5.34 |
| | 20 μg/ml | 4.58 |

*I Crude preparation, Weizmann Institute of Science
**II Purified peptide, Bachem.

As can be seen in Table 3B below, similar results were obtained with the following peptides:

A—Thrombin receptor (42–55), human Ser-Phe-Leu-Leu-Arg-Asn-Pro-Asn-Asp-Lys-Tyr-Glu-Pro-Phe (SEQ ID NO: 1)

B—Thrombin receptor (42–47), human Ser-Phe-Leu-Leu-Arg-Asn (1–6 of SEQ ID NO: 1)

C—Thrombin receptor (42–55), hamster Ser-Phe-Phe-Leu-Arg-Asn-Pro -Gly-Glu-Asn-Thr-Phe-Glu-Leu (SEQ ID NO: 2)

D—Thrombin receptor (42–47), hamster Ser-Phe-Phe-Leu-Arg-Asn (1–6of SEQ ID NO: 2) all from Neosystem, France.

TABLE 3B

| Additive to basic SFM | | IL-6 (μg/ml) |
|---|---|---|
| None | | 2.17 |
| TRA II (from Table 3A) | 5 μg/ml | 4.29 |
| | 1.25 μg/ml | 3.63 |
| A | 5 μg/ml | 2.27 |
| | 1.25 μg/ml | 4.21 |
| B | 5 μg/ml | 4.32 |
| | 1.25 μg/ml | 4.32 |
| C | 5 μg/ml | 4.13 |
| | 1.25 μg/ml | 4.06 |
| D | 5 μg/ml | 5.04 |

TABLE 3B-continued

| Additive to basic SFM | IL-6 (µg/ml) |
|---|---|
| 1.25 µg/ml | 4.89 |

EXAMPLE 8:

To examine the activity of the peptide under production conditions, a 1-liter spinner with disc-carriers was connected to CelliGen bioreactor controls. Cells of TBP clone 108-1-22-12/4 were seeded and after a growth period, production was initiated with 2% FBS.

Figure 10:
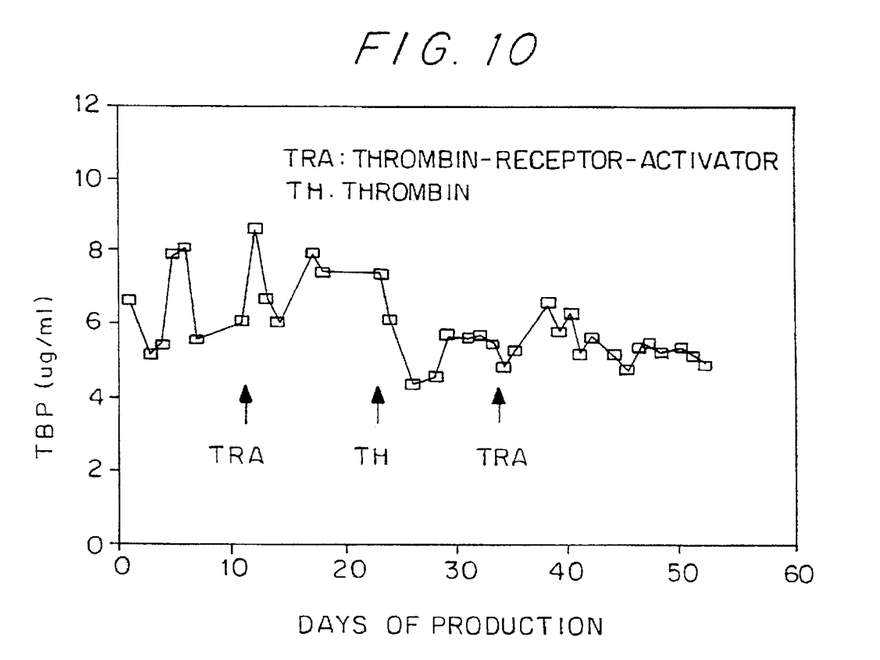
FIG. 10 illustrates TBP production in a 1 liter bioreactor.

Ten days later the serum supplement production medium was replaced by SFM containing corn gluten hydrolysate, insulin and TRA. Production continued for 40 days. During part of the production time, TRA was replaced with thrombin. Replacement of thrombin by TRA did not affect the production level (FIG. 10).

EXAMPLE 9: Cloning and expression of thrombin and insulin in CHO cells

After initial cloning of the cDNAs coding for thrombin and insulin in a conventional manner, the DNA fragments containing the sequence coding for the mature proteins fused to a signal peptide are isolated. The signal peptide may either be their own or a signal peptide which is properly secreted in CHO cells. Thereafter expression vectors containing these DNA fragments fused to a promoter for expression in CHO cells, such as SV 40 or CMV, are constructed.

The expression vector is now transfected into one of the CHO clones used for recombinant production of the desired protein, using a second type of selection, e.g. gentamycin (G418). Insulin and thrombin are secreted in the serum-free medium and thus support heterologous protein production and secretion by the CHO clones.

REFERENCES

Awbrey, B. L, Hoak, J. C., and Owen, W. G. Binding of human thrombin to cultured human endothelial cells, *J. Biol. Chem.* 254: 4092 (1979).

Barnes, D, and Sam, G. Serum-free cell culture: A unifying approach. *Cell* 22: 649–655 (1980).

Barnes, D. W., Sirbasku, D. A., and Solo, G. H. *Cell culture methods for molecular and cellular biology.* Vols. 1–4, Liss, New York (1984).

Barnes, D. Serum-free animal cell culture. *Bio Techniques* 5: 534–542 (1987).

Bauer, P. I., Machovich, R., Aranyi, P., Buki, K., Csonka, E., and Horvath, I., Mechanism of thrombin binding to endothelial cells. *Blood* 61: 368 (1983).

Broad, D., Boraston, R, and Rhodes M. Production of recombinant proteins in serum-free media. *Cytotechnology* 5: 47–55 (1991).

Chen, L. B. Thrombin as a growth factor for cultured cells. "*The growth requirements of vertebrate cells in vitro.*" Eds. Waymouth C., Ham, R. G., Chapple, P. J., Cambridge University Press, pp. 380–387 (1981).

Chernajovsky, Y., Mory, Y., Chen, L., Marks, Z., Novick, D., Rubinstein, M, and Revel, M. Efficient constitutive production of human fibroblast interferon by hamster cells transformed with the IFN-β gene fused to an SV40 early promoter. *DNA* 3: 297–307 (1984).

Cunningham, D. D., Carney, D. H. and Glenn, K. C., A cell-surface component involved in thrombin-stimulated call division. *Hormones and Celt Culture.* Eds. Sato, G. H., and Ross, R., Cold Spring Harbor, New York, 199 (1979).

Familletti P. C., and Fredericks, J. E. Techniques for mammalian cell immobilization. *Bio/Technology* 6: 41–44 (1988).

Glenn, K. C, Karney, D. H., Fenton, II J. W., and Cunningham, D. D., Thrombin active site regions required for fibrinoblast receptor binding and initiation of cell division. *J. Biol. Chem.* 285: 6609 (1980).

Grace, T. D. L. Establishment of four strains of cells from insect tissues gown in vitro. *Nature* 195: 788–789 (1962).

Hink, W. F. A serum-free medium for the culture of insect cells and production of recombinant proteins. *In Vitro Cell Dev. Biol.* 27A: 397–401. (1991).

Jayme, D. W. Nutrient optimization for high density biological production applications. *Cytotechnology* 5: 15–30 (1991).

Loskutoff, D. Effect of thrombin on the fibrinolytic activity of cultured bovine endothelial cells. *J. Clin. Invest.* 64, 329 (1979).

Machovich, R. and Csonka, E. Mechanism of the binding of thrombin endothelial cells. *Acta Biochim. Biophys. Acad. Sci. Hung.* 17: 66 (Abstr.) (1982).

Marino, M. H., expression systems for heterologous protein production. *Bio Pharm.* Jul/Aug: 18–33 (1989).

Morita, M., and Iwanaga, S. Prothrombin activator from Echis carinatus venom. *Methods in Enzymology* 80: 303–311 (1981).

Mosher, D. F. and Vaheri, A. Thrombin simulates the production and release of a major surface-associated glycoprotein (fibronectin) in cultures of human Fibroblast. *Exp. Cell Res.* 112: 323 (1978).

Owen, W. G. and Esrnon, C. T. Functional properties of an endothelial cell cofactor for thrombin catalyzed activation of protein C. *J. Biol. Chem.* 256: 5532 (1981).

Sato, G. H., Pardee A. B., and Sirbasku, D. A. *Growth of cells in hormonally-defined media. Books A and B.* Cold Spring Harbor, New York (1982).

Taub, M. *Tissue Culture of Epithelial Cells.* Plenum, New York (1985).

Vu, T. K. H., Hung, D. T., Wheaton, V. L, and Coughlin, S. R. Molecular cloning of a functional thrombin receptor reveals a novel proteolytic mechanism of receptor activation. *Cell* 64: 1057–1068 (1991).

Weiss, S. A., Lester, T. L., Kalter, S. S., and Heberling, R. L. Chemically defied serum-free media for the cultivation of primary cells and their susceptibility to viruses. *In Vitro* 16: 616–628 (1980).

Weksler, B. B., Ley, C. W., and Jaffe, E. A. Stimulation of endothelial cell prostacyclin ($PGI_2$) production by thrombin, trypsin and ionophore A231817. *J. Clin. Invest.* 62: 923 (1978).

Workman, E. F., White, G. C., and Lundblad, R. L. High affinity binding of thrombin to platelets. Inhibition by tetranitromethane and heparin *Biochem. Biophys. Res. Commun.* 75: 925 (1977).

Zetter, B. R., Chen, L. B., and Buchanan, J. M. Binding and internalization of thrombin by normal and transformed chick cells. *Proc. Natl. Acad. Sci., U.S.A.* 74: 596 (1977).

What is claimed is:

1. A serum-free medium for mammalian cells, consisting essentially of a basic medium selected from the group consisting of DMEM, F12, RPM1 1640, and mixtures thereof, to which has been added     a cell viability protection agent selected from the group consisting of ADC-1, a protein hydrolysate, and methyl cellulose,     insulin, and     a cell activator which is either thrombin or a thrombin receptor activator.

2. A serum-free medium for mammalian cells according to claim 1, wherein the protein hydrolysate is lactalbumin hydrolysate.

3. A serum-free medium for mammalian cells according to claim 1, wherein the protein hydrolysate is corn gluten hydrolysate.

4. A serum-free medium for mammalian cells according to claim 1, wherein said cell activator is thrombin.

5. A serum-free medium for mammalian cells according to claim 4, wherein said thrombin is a recombinant thrombin.

6. A serum-free medium for mammalian cells according to claim 1, wherein said cell activator is a thrombin receptor activator.

7. A serum-free medium for mammalian cells according to claim 6, wherein said thrombin receptor activator is a recombinant thrombin receptor activator.

8. A serum-free medium for mammalian cells according to claim 6, wherein the thrombin receptor activator is a peptide having the amino acid sequence Ser-Phe-Leu-Leu-Arg-Asn-Pro-Asn-Asp-Lys-Tyr-Glu-Pro-Phe (SEQ ID NO: 1).

9. A serum-free medium for mammalian cells according to claim 6, wherein the thrombin receptor activator is a peptide having the amino acid sequence Ser-Phe-Leu-Leu-Arg-Asn (1–6 of SEQ ID NO: 1).

10. A serum-free medium for mammalian cells according to claim 6, wherein said thrombin receptor activator is in an amount between 1 µg/ml and 20 µg/ml.

11. A serum-free medium for mammalian cells according to claim 1, wherein said insulin is a recombinant insulin.

12. A serum-free medium for mammalian cells according to claim 1, wherein: said insulin is in an amount between 0.1 µg/ml and 2 µg; and said thrombin is in an amount between 0.01 µg/ml and 2 µg/ml.

13. A method for obtaining a recombinant protein, comprising:

cultivating in a serum-free medium in accordance with claim 1 a mammalian cell line capable of expressing the recombinant protein under conditions suitable to obtain expression of said recombinant protein; and     isolating the recombinant protein produced in said cultivating step.

14. A serum-free medium for mammalian cells, consisting of a basic medium selected from the group consisting of DMEM, F12, RPM1 1640, and mixtures thereof, to which has been added     a cell viability protection agent selected from the group consisting of ADC-1, a protein hydrolysate, and methyl cellulose,     insulin, and     a cell activator which is either thrombin or a thrombin receptor activator.

15. A method for the preparation of a recombinant protein in mammalian cells, comprising:

providing recombinant mammalian cells capable of expressing the recombinant protein and also capable of expressing at least one member selected from the group consisting of insulin, thrombin and a thrombin receptor activator; and growing said cells on a serum-free production medium consisting essentially of:
- a basic medium selected from the group consisting of DMEM, F12, RPM1 1640, and mixtures thereof,
- a cell viability protection agent selected from the group consisting of ADC-1, a protein hydrolysate, and methyl cellulose,
- insulin, if said cells are not capable of expressing insulin, and
- either thrombin or a thrombin receptor activator, if said cells are incapable of expressing either thrombin or a thrombin receptor activator.

16. A method in accordance with claim 15, wherein said cells are capable of expressing insulin.

17. A method in accordance with claim 15, wherein said cells are capable of expressing thrombin.

18. A method in accordance with claim 15, wherein said cells are capable of expressing a thrombin receptor activator.

19. A method in accordance with claim 15, wherein said cells are capable of expressing insulin as well as at least one of thrombin and a thrombin receptor activator.

20. A method in accordance with claim 15, wherein said mammalian cells are Chinese hamster ovary cells.

21. A method in accordance with claim 15, further including the step of isolating said recombinant protein produced in said growing step.

22. A serum-free medium for mammalian cells, comprising:

a basic medium;

a cell viability protection agent;

insulin; and a thrombin receptor activator which is a peptide having the amino acid sequence of SEQ ID NO: 2.

23. A serum-free medium for mammalian cells, comprising:

a basic medium;

a cell viability protection agent;

insulin; and a thrombin receptor activator which is a peptide having the amino acid sequence of residues 1–6 of SEQ ID NO: 2.

* * * * *